(12) United States Patent
Suzuki et al.

(10) Patent No.: US 9,897,519 B2
(45) Date of Patent: Feb. 20, 2018

(54) AUTOMATIC ANALYZER AND METHOD FOR WASHING SAMPLE-PIPETTING PROBE

(71) Applicant: HITACHI HIGH-TECHNOLOGIES CORPORATION, Tokyo (JP)

(72) Inventors: Naoto Suzuki, Tokyo (JP); Yoshiaki Saito, Tokyo (JP); Yoichi Aruga, Tokyo (JP); Toshihide Orihashi, Tokyo (JP); Kazuhiro Nakamura, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 336 days.

(21) Appl. No.: 14/366,079

(22) PCT Filed: Dec. 14, 2012

(86) PCT No.: PCT/JP2012/082561
§ 371 (c)(1),
(2) Date: Jun. 17, 2014

(87) PCT Pub. No.: WO2013/099660
PCT Pub. Date: Jul. 4, 2013

(65) Prior Publication Data
US 2014/0363896 A1 Dec. 11, 2014

(30) Foreign Application Priority Data

Dec. 26, 2011 (JP) .................................. 2011-284472

(51) Int. Cl.
*G01N 1/34* (2006.01)
*G01N 35/10* (2006.01)
(Continued)

(52) U.S. Cl.
CPC .......... *G01N 1/34* (2013.01); *G01N 35/00584* (2013.01); *G01N 35/1004* (2013.01); *G01N 2001/002* (2013.01); *Y10T 436/25125* (2015.01)

(58) Field of Classification Search
None
See application file for complete search history.

(56) References Cited

U.S. PATENT DOCUMENTS 5,415,840 A 5/1995 Sano et al.
5,468,453 A * 11/1995 Holt .................... B01L 3/0275
422/509

(Continued)

FOREIGN PATENT DOCUMENTS

CN 1053682 A 8/1991
EP 1443329 A2 8/2004
(Continued)

OTHER PUBLICATIONS

International Preliminary Report on Patentability received in International Application No. PCT/JP2012/082561 dated Jul. 10, 2014.
(Continued)

*Primary Examiner* — Jill A Warden
*Assistant Examiner* — Benjamin R Whatley
(74) *Attorney, Agent, or Firm* — Mattingly & Malur, PC (57) ABSTRACT

When the type is to be changed from serum (preceding sample) to urine (current sample), "serum" is set to a preceding type and "urine" is set to a measurement type at number 1 in a condition number. At condition number 1, the wash type is pattern 1, with washing performed once with detergent 1. Where the preceding sample is serum and the current sample is CSF, the condition number is 2 and the wash type is pattern 2, with washing performed twice using detergent 1 and once with detergent 2. Where the preceding
(Continued)

sample is urine and the current sample is CSF, the condition number is 3 and the wash type is pattern 3, with washing performed once with detergent 1, once with detergent 2, and once with water. In the case of pattern 4, washing is performed three times with detergent 1.

5 Claims, 9 Drawing Sheets (51) Int. Cl.
*G01N 35/00* (2006.01)
*G01N 1/00* (2006.01)

(56) References Cited

U.S. PATENT DOCUMENTS

| | | | |
|---|---|---|---|
| 5,559,002 A | 9/1996 | Uzan et al. | |
| 5,610,069 A | 3/1997 | Clark et al. | |
| 6,752,960 B1* | 6/2004 | Matsubara | G01N 35/1004 422/552 |
| 2003/0223472 A1* | 12/2003 | Ravalico | G01N 35/1004 374/31 |
| 2004/0096931 A1* | 5/2004 | Kawashima | G01N 35/1004 435/34 |
| 2004/0102997 A1* | 5/2004 | Kikuchi | G01N 35/00663 422/62 |
| 2005/0074363 A1* | 4/2005 | Dunfee | G01N 35/1004 422/81 |
| 2006/0177344 A1* | 8/2006 | Ouchi | G01N 35/1002 422/64 |
| 2006/0293200 A1* | 12/2006 | Takayama | C11D 1/72 510/223 |
| 2008/0099057 A1* | 5/2008 | Dunfee | B08B 3/022 134/94.1 |
| 2009/0032064 A1* | 2/2009 | Gifford | B01L 99/00 134/18 |
| 2009/0114538 A1* | 5/2009 | Takayama | G01N 35/00722 204/407 |
| 2009/0306300 A1* | 12/2009 | Taniguchi | B01L 3/508 525/240 |
| 2010/0126286 A1* | 5/2010 | Self | G01N 35/04 73/863.81 |
| 2011/0171069 A1* | 7/2011 | Mishima | G01N 35/1004 422/68.1 |
| 2011/0236990 A1* | 9/2011 | Mizutani | G01N 35/00603 436/180 |
| 2012/0003731 A1* | 1/2012 | Kuroda | G01N 35/00732 435/288.7 |

FOREIGN PATENT DOCUMENTS

| | | | | |
|---|---|---|---|---|
| JP | 6-27944 A | 2/1994 | | |
| JP | 09-503060 A | 3/1997 | | |
| JP | 2000-046844 A | 2/2000 | | |
| JP | 2005-527839 A | 9/2005 | | |
| JP | 2009-041961 A | 2/2009 | | |
| JP | 2009-293939 A | 12/2009 | | |
| JP | 2010-216876 A | 9/2010 | | |
| JP | 2011-220928 A | 11/2011 | | |
| JP | 2011-227065 A | 11/2011 | | |
| WO | WO 9508774 A2 * | 3/1995 | | B01F 11/0022 |
| WO | 2010/104072 A1 | 9/2010 | | |
| WO | 2014/017275 A1 | 1/2014 | | |

OTHER PUBLICATIONS

Chinese Office Action received in corresponding Chinese Application No. 201280064404.6 dated Jan. 12, 2015.
Extended European Search Report received in corresponding European Application No. 12861863.4 dated Aug. 26, 2015.
Japanese Office Action received in corresponding Japanese Application No. 2016-248171 dated Oct. 24, 2017.

* cited by examiner

SETUP SCREEN OF WASHING TO AVOID CARRY-OVER OF EACH SAMPLE TYPE

| CONDITION NO. (201) | PRECEDING SAMPLE TYPE (202) | SAMPLE TYPE TO BE MEASURED (203) | WASH TYPE (204) |
|---|---|---|---|
| 1 | SERUM | URINE | PATTERN 1 |
| 2 | SERUM | CSF | PATTERN 2 |
| 3 | URINE | CSF | PATTERN 3 |
| 4 | — | — | — |
| 5 | — | — | — |
| 6 | — | — | — |
| 7 | — | — | — |
| 8 | — | — | — |
| 9 | — | — | — |
| 10 | — | — | — |
| 11 | — | — | — |
| 12 | — | — | — |

(B)

205

EDIT SCREEN OF WASH PATTERNS TO AVOID CARRY-OVER OF EACH SAMPLE TYPE

| WASH TYPE | WASH CYCLE USING DETERGENT 1 | WASH CYCLE USING DETERGENT 2 | WASH CYCLE USING WATER |
|---|---|---|---|
| PATTERN 1 | 1 | 0 | 0 |
| PATTERN 2 | 2 | 1 | 0 |
| PATTERN 3 | 1 | 1 | 1 |
| PATTERN 4 | 3 | 0 | 0 |

SETUP SCREEN OF WASHING TO AVOID CARRY-OVER OF EACH SAMPLE TYPE

| CONDITION NO. | PRECEDING SAMPLE TYPE | SAMPLE TYPE TO BE MEASURED | WASH TYPE | THE NUMBER OF WATER WASHING AVOIDED |
|---|---|---|---|---|
| 1 | SERUM | URINE | PATTERN 1 | 2 |
| 2 | SERUM | CSF | PATTERN 2 | 0 |
| 3 | URINE | CSF | PATTERN 3 | 0 |
| 4 | — | — | — | — |
| 5 | — | — | — | — |
| 6 | — | — | — | — |
| 7 | — | — | — | — |
| 8 | — | — | — | — |
| 9 | — | — | — | — |
| 10 | — | — | — | — |
| 11 | — | — | — | — |
| 12 | — | — | — | — |

(B)

EDIT SCREEN OF WASH PATTERNS TO AVOID CARRY-OVER OF EACH SAMPLE TYPE

| WASH TYPE | WASH CYCLE USING DETERGENT 1 | WASH CYCLE USING DETERGENT 2 | WASH CYCLE USING WATER |
|---|---|---|---|
| PATTERN 1 | 1 | 0 | 0 |
| PATTERN 2 | 2 | 1 | 0 |
| PATTERN 3 | 1 | 1 | 1 |
| PATTERN 4 | 3 | 0 | 0 |

CONTROL ON PIPETTING OVER SAMPLE PROBE FOR SAMPLE PIPETTING (THE CASE WHERE IT IS DETERMINED WHETHER WASHING IS NECESSARY DEPENDING ON THE NUMBER OF TIMES WASHING IS PERFORMED WITH WATER WHERE PIPETTING IS NOT CONTINUOUS)

(B)

| SAMPLE TYPES TO BE INTRODUCED AND ORDER IN WHICH SAMPLES ARRIVE AT PIPETTING POSITION | | |
|---|---|---|
| ORDER OF ARRIVAL | SAMPLE NAME | TYPE |
| 1ST | SAMPLE 1 | SERUM |
| 2ND | SAMPLE 2 | SERUM |
| 3RD | SAMPLE 3 | URINE |

AUTOMATIC ANALYZER AND METHOD FOR WASHING SAMPLE-PIPETTING PROBE

TECHNICAL FIELD

The present invention relates to an automatic analyzer that performs quantitative and qualitative analyses on biological samples of a plurality of types such as blood, urine, and CSF (cerebrospinal fluid).

BACKGROUND ART

There is an automatic analyzer to measure biological samples of multiple types such as blood (including serum and plasma), urine, and CSF (cerebrospinal fluid) with a sample-pipetting probe shared between the samples. It is general practice to use water to wash the sample-pipetting probe after pipetting and to subsequently rinse inner and outer walls of these automatic analyzers in order to prevent carry-over between the samples.

There conventionally have been attempts to reduce the carry-over between pipetted samples by way of improving the method for washing the nozzle and the rinse bath in which to wash the nozzle as one of the techniques for washing the sample-pipetting nozzle.

Meanwhile, the automatic analyzers have been requested to improve their analytical processing capability in recent years, and the time to pipette samples has been attempted to be shorter so as to boost overall analytical processing performance.

The time to wash the sample-pipetting nozzle also has been shortened as a result, which can lead to cases where it may be difficult to avoid carry-over unfailingly between samples following an ordinary washing operation especially in measurement items susceptible to the effects of carry-over.

The existing technologies for avoiding the carry-over between samples include a technique for setting up whether to insert a washing operation of the sample-pipetting nozzle for each measurement item and actually insert the nozzle operation before a sample is pipetted for measurement of the item in question.

Patent Document 1 discloses washing controls according to which a special washing process is performed to prevent contamination between the samples with the use of the biochemical measuring device with regard to highly sensitive immunological items if a specific analysis item is contained in individual samples in a device structure having a device for measuring biochemical items connected with a device for measuring immunological items.

PRIOR ART DOCUMENT

Patent Document

Patent Document 1: JP-2000-46844-A

SUMMARY OF THE INVENTION

Problem to be Solved by the Invention

In the case of an analysis item where each type has greatly different concentration, however, carry-over might occur at the time of switchover between sample types.

For example, the normal concentration of GLU (blood glucose) contained in a serum sample is from 70 to 109 [mg/dL], whereas that of GLU in a urine sample is from 1 to 2 [mg/dL]. The concentration found in samples differs significantly between different analysis items.

For this reason, the effects of carry-over between samples of the same type are negligible even if an infinitesimal amount of a sample remains on the inner wall of the sample-pipetting nozzle. At the time of switchover from a sample of a high-concentration type to a sample of a low-concentration type, there can be significant effects of carry-over between the samples even if only a very small amount of the sample remains, which could affect the results of measurements.

The automatic analyzers of recent years have been required to deal with ever-smaller amounts of samples. This has created the possible effects of carry-over greater than ever on the result of measurement of small amounts of samples.

It is possible to prevent the effects of carry-over between samples with the above-mentioned method for determining whether to insert the washing operation for each measurement item by setting up the washing operation for any vulnerable measurement item, so that the washing operation will be inserted at the time of switchover to the target type.

The washing operation will be inserted for samples of an unsusceptible type or for consecutive samples of the same type as well at the same time, pushing up running costs and lowering the efficiency of analyses due to detergents and water wasted.

The use of the method described in Patent Document 1 will prevent the wasteful insertion of the washing operation as above through the washing control being set only to the first sample that is to start the target type.

The insertion of a time-critical sample of different type into a sequence of samples of the same type, however, could affect the samples that have not had their washing control set.

The interruption by the time-critical samples of a different type occurs on an irregular basis and is difficult to predict at the time of the setup.

The present invention has been made in view of the above circumstances, and an object of the invention is to provide an automatic analyzer and a method for washing a sample-pipetting probe, whereby the carry-over between low-concentration samples of different types can be suppressed with a minimum of washing operations so as to improve the accuracy of the results of measurements regardless of the order in which samples are introduced or the order in which the samples reach the pipetting position.

Means for Solving the Problem

In order to achieve the above object, the present invention is structured as follows:

There is provided an automatic analyzer including: a reagent container conservation mechanism which holds a reagent container housing a reagent; a reaction vessel conservation mechanism which holds a reaction vessel; a reagent-pipetting probe which pipettes the reagent held in the reagent container into the reaction vessel; a sample-pipetting probe which pipettes a sample to be measured into the reaction vessel; a spectrophotometer which analyzes the sample in the reaction vessel; and a rinse bath in which the sample-pipetting probe is washed. Where the sample-pipetting probe pipettes samples of different types consecutively into the reaction vessel, a method of washing the sample-pipetting probe is determined before the next sample is pipetted on the basis of the combination of the type of the sample currently pipetted and the type of the next sample to be pipetted, and then the sample-pipetting probe is washed with the rinse bath.

Effect of the Invention

According to the present invention, it is possible to implement an automatic analyzer and a method of washing a sample-pipetting probe, whereby the carry-over between low-concentration samples of different types can be suppressed with a minimum of washing operations so as to improve the accuracy of the results of measurements regardless of the order in which samples are introduced or the order in which the samples reach the pipetting position.

MODE FOR CARRYING OUT THE INVENTION

One embodiment of the present invention is explained below with reference to the accompanying drawings.

The embodiment explained hereunder is only one of examples of the present invention and is not limited to the example here.

Embodiment

Figure 1:
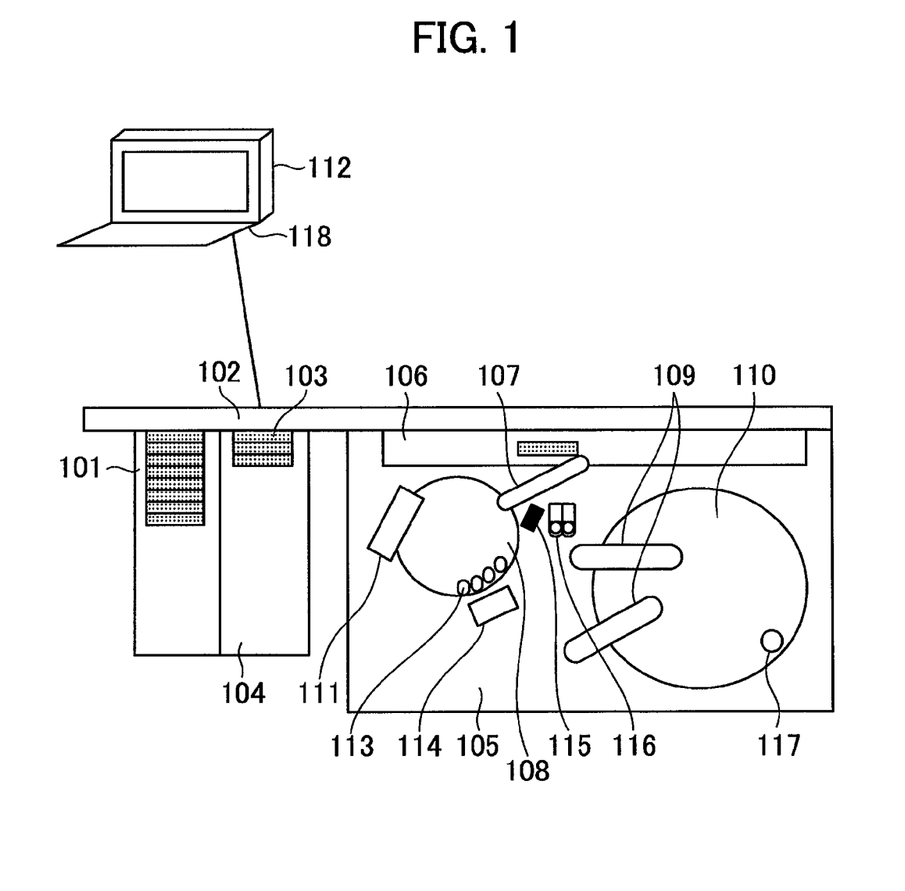
FIG. 1 is an overall configuration diagram of an automatic analyzer to which one embodiment of the present invention is applied.

FIG. 1 is an overall structure diagram of an automatic analyzer to which one embodiment of the present invention is applied.

In FIG. 1 the automatic analyzer includes a personal computer 112. A request to analyze a sample is registered through a keyboard (input mechanism) 118 of the personal computer 112. The automatic analyzer also includes an analysis module 105 for analyzing samples. A reaction vessel 113 is placed on a reaction disk 108 of the analysis module 105. The entire reaction disk 108 is maintained at a predetermined temperature in a heat retaining device.

A sample placed on a sample rack 108 mounted on a sample feeding part 101 is transferred via a sample feeder line 102 to a pipetting line 106 inside the analysis module 105. The personal computer 112 controls the operation of the pipetting line 106 to move the sample rack 103 up to a sample-pipetting position where a sample probe (sample-pipetting probe) 107 pipettes the sample.

The sample placed on the rack 103 is pipetted in a predetermined amount into the reaction vessel 113 with the use of the sample probe (sample-pipetting probe) 107 in accordance with analysis parameters stored in a memory of the personal computer 112 and in keeping with the request to analyze the sample.

The reaction vessel 113 into which the sample has been pipetted is subsequently transferred to a reagent-pipetting position as a result of the reaction vessel 108 being rotated.

A reagent container 117 filled with the reagent for mixture and reaction with samples is installed inside a reagent disk 110. In accordance with the analysis parameters stored in the memory of the personal computer 112, the reagent is aspirated from within the reagent container 117 and pipetted in a predetermined amount into the reaction vessel 113 on the reaction disk 108 using a reagent-pipetting probe 109.

Thereafter, a stirring mechanism 111 stirs the sample and the reagent to make a mixture.

When the reaction vessel 113 traverses a photometry position on the reaction disk 108 a multi-wavelength photometer 114 measures absorbance. The measured absorbance is converted to concentration data.

According to the above-described principle of measurement, the user can set various parameters necessary for measurement, register samples to be measured, and verify the results of measurements using the keyboard 118 and the display screen of the personal computer 112.

As a general device structure for washing of the sample probe 107 of the present invention, there are provided a rinse bath 115 and a wash fluid bath 116 on a rotary trajectory of the sample probe 107, the rinse bath 115 being used for washing with water following pipetting of the sample, the wash fluid bath 116 being used for special washing of the sample probe 107. The wash fluid bath 116, including a plurality of baths to accommodate a plurality of types of wash fluids, may have a single bath when only one type of wash fluid is used. Reference numeral 104 indicates a sample storage.

Explained next is how the sample-pipetting probe of the embodiment of the present invention is washed.

Figure 2:
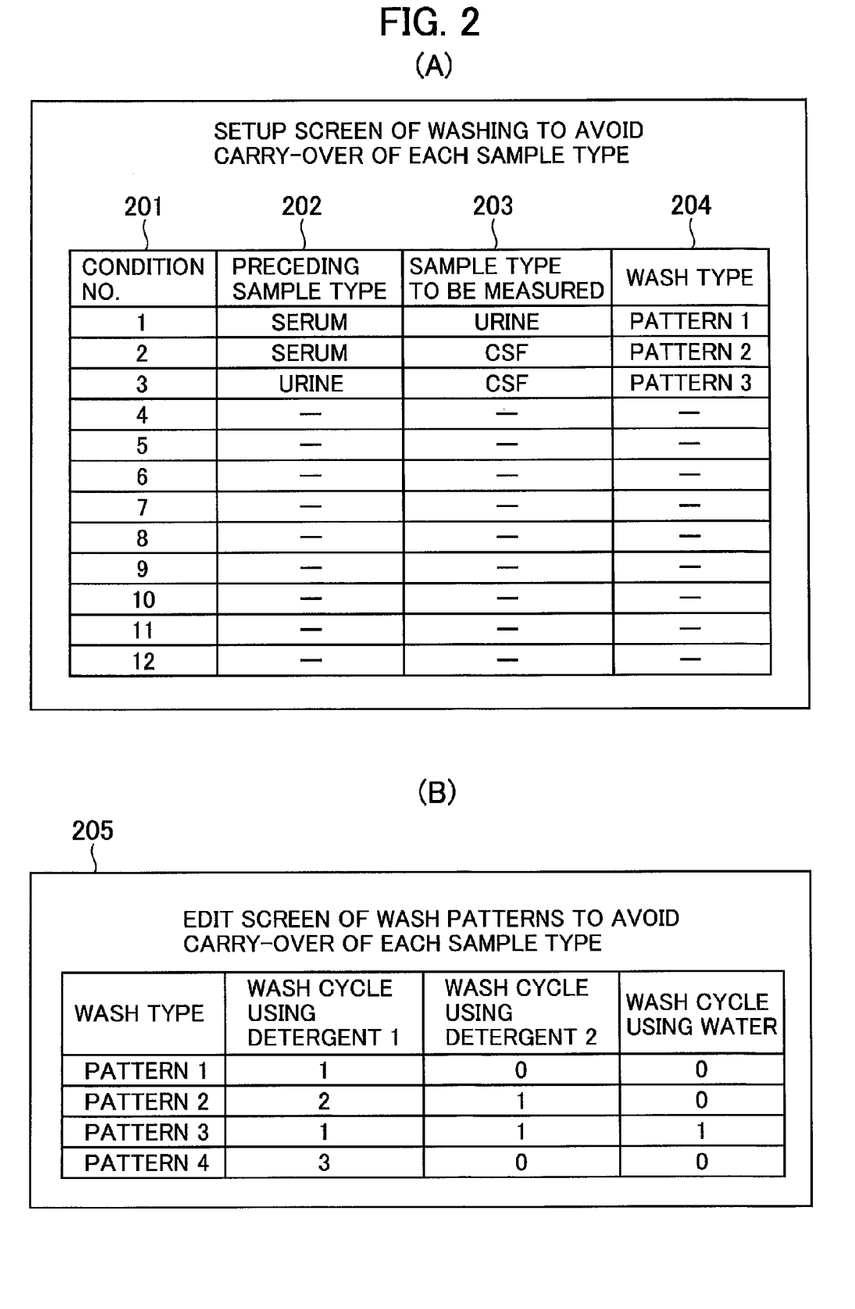
FIG. 2 is a diagram showing screen examples in which to set whether to insert a special washing operation.

FIG. 2 shows screen examples in which to set whether to insert a special washing operation between different types, the operation being performed to prevent carry-over between samples of the different types. This screen is a display screen of the personal computer 112.

FIG. 2(A) shows a screen on which to set a wash type with regard to the relations between the type of the sample about to be pipetted (the next sample to be pipetted) and the type of the sample that was measured previously (the preceding sample pipetted). Subfigure (B) in FIG. 2 shows a screen on which to edit washing methods by wash type.

In FIG. 2(A), "serum" is set to a preceding type (202) and "urine" is set to a measurement type (203) at No. 1 in a condition number field (201) where the type switches from serum (preceding sample) to urine (current sample) and where the range of concentration of an ingredient in samples varies between them such that the concentration of the ingredient in the urine sample can be affected.

Upon detecting that sample types have been set, the personal computer 112 of the automatic analyzer generates an optimum wash pattern for removing the carry-over from the pipetting nozzle on the basis of the relations between the set types and of the device characteristics, and recommends the pattern as an initial setting {(B) in FIG. 2}. At condition No. 1, the wash type is pattern 1 involving the use of wash fluid 1 and a cleaning frequency of 1.

The wash patterns are each composed of wash fluids (including detergent and water) and the frequency of washing using the wash fluids. The patterns can be changed by the user on a wash pattern edit screen (205) through the keyboard (input mechanism) 118. The wash type setup screen shown in FIG. 2(A) can also be changed with the keyboard (input mechanism) 118.

In this manner, settings should be made in similar procedures if there exist combinations of sample types that can affect subsequent samples.

Other examples shown in FIGS. 2(A) and (B) include the case at condition No. 2 with wash pattern 2 in which the preceding sample is serum and the current sample is CSF. In this case, the probe is washed twice with detergent 1 and once with detergent 2. Also included is the case at condition No. 3 with wash pattern 3 in which the preceding sample is urine and the current sample is CSF. In this case, the probe is washed once with detergent 1, once with detergent 2, and once with water.

In the case of pattern 4, the probe is washed three times with detergent 1.

Figure 3:
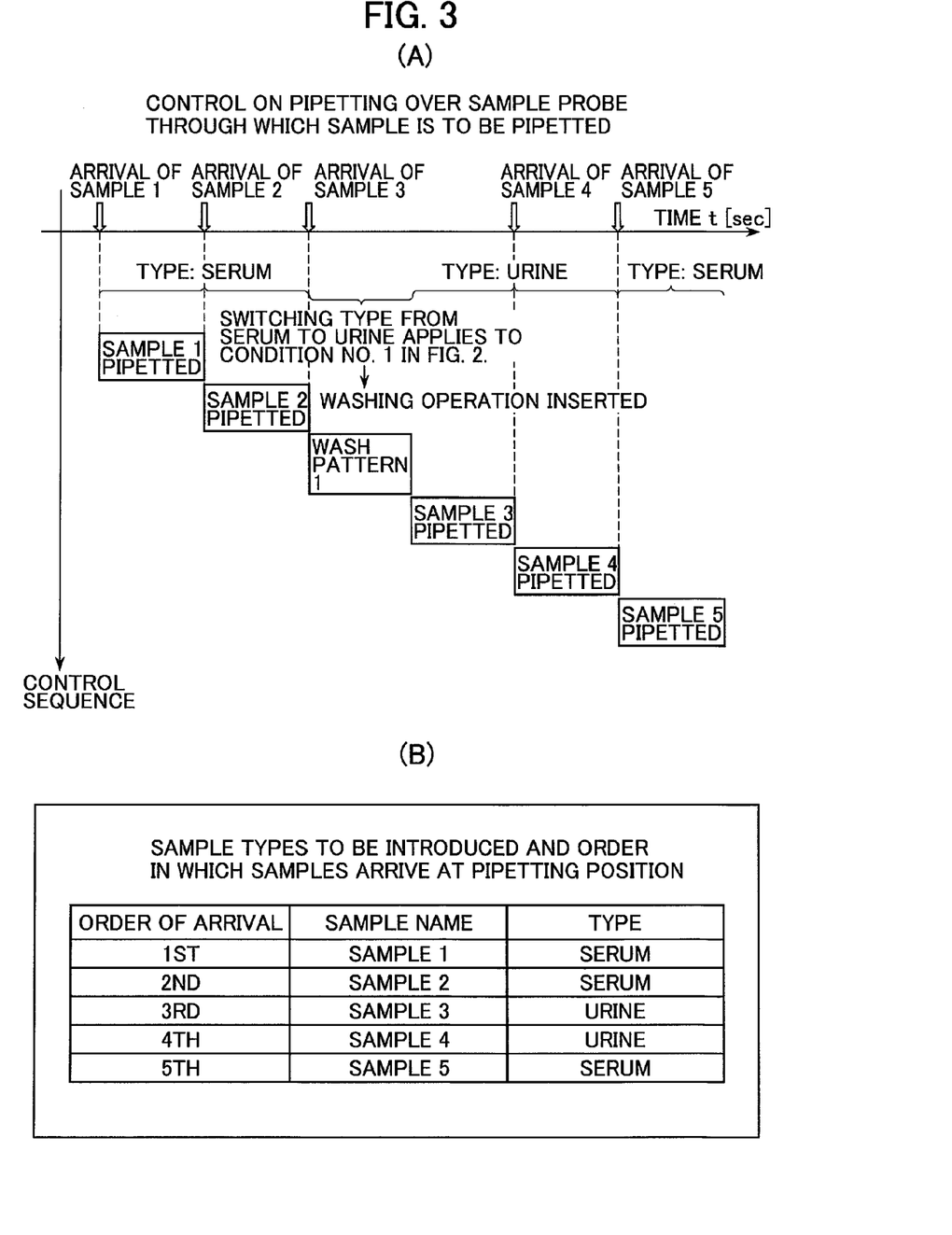
FIG. 3 is a diagram chronologically showing how the sample-pipetting probe is controlled on the basis of the sample type and the order in which samples arrive.
Figure 4:
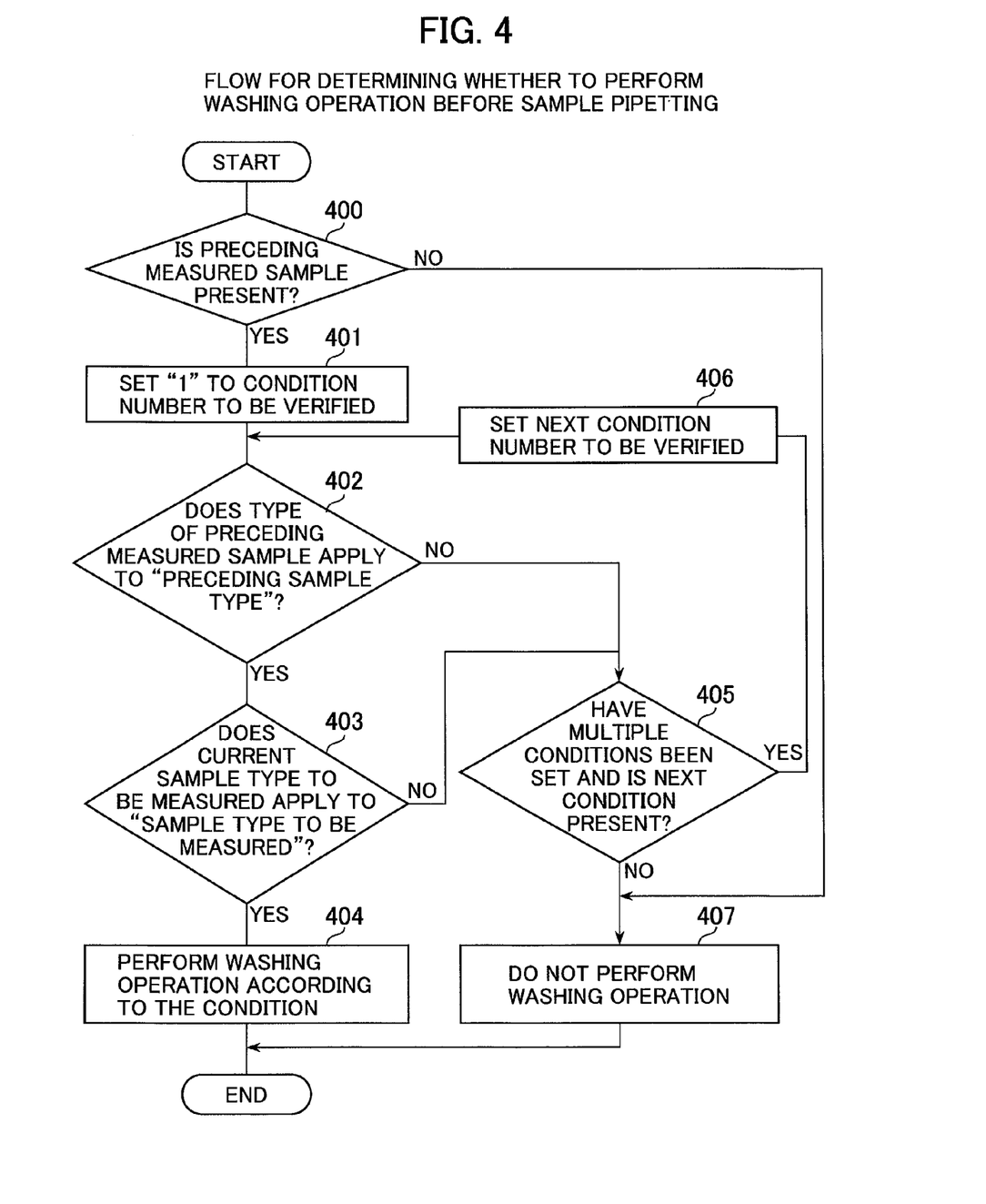
FIG. 4 is a flowchart of processing for determining whether to insert the washing operation to prevent carry-over between samples.
Figure 5:
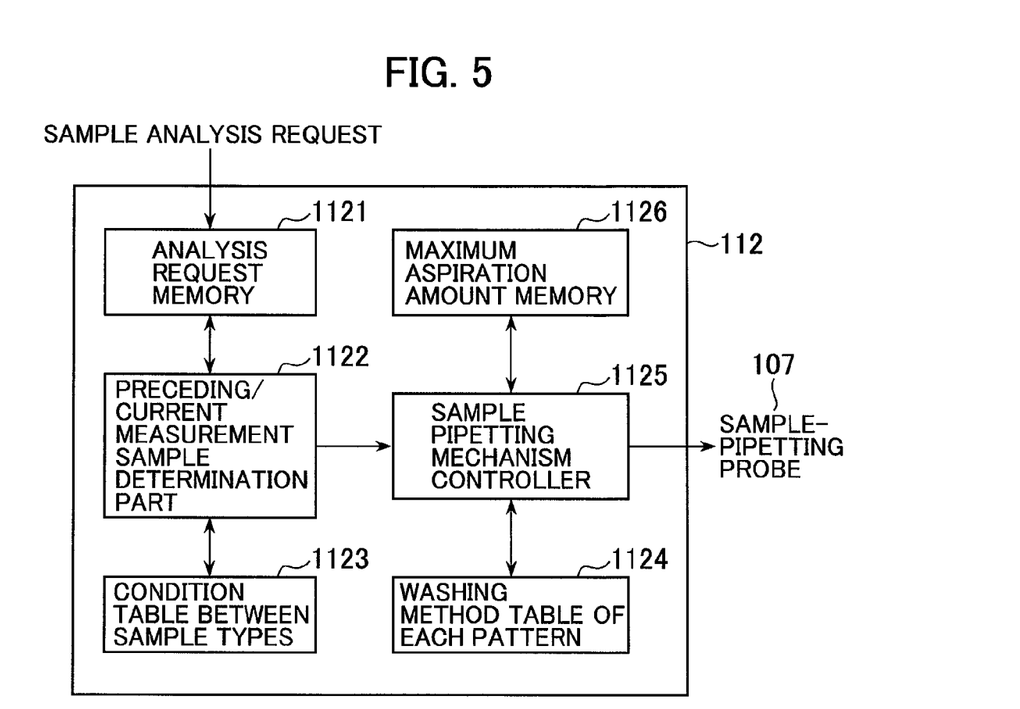
FIG. 5 is a functional block diagram for controlling the washing operation on the sample-pipetting probe.

Explained next with the use of FIGS. 3, 4, 5 is how to control the washing operation of the sample probe 107 during measurement in accordance with the settings in FIG. 2.

FIG. 3 is a diagram chronologically showing how the sample probe 107 for pipetting samples is controlled on the basis of the sample type and the order in which the samples arrive during measurement.

FIG. 4 is a flowchart of processing for verifying the settings in FIG. 2 before the sample that has arrived starts to be pipetted and for determining whether to insert the washing operation to prevent carry-over between the different sample types.

FIG. 5 is a functional block diagram of a controller of the personal computer 112 for controlling the washing operation on the sample-pipetting probe 107. The personal computer 112 includes an analysis request memory 1121 that chronologically stores the types of the samples requested to be analyzed, a preceding/current measurement request determination part 1122, a condition table between sample types 1123 that stores the information set on the wash type setup screen shown in FIG. 2(A), a washing method table of each pattern (washing method table of each wash type) 1124 that stores the washing methods set by wash type as shown in FIG. 2(B), a sample-pipetting mechanism controller 1125, and a maximum aspiration amount memory 1126.

Once the automatic analyzer starts sample measurement, samples are transferred to the sample-pipetting position of the sample-pipetting probe 107 via feeder lines (101, 102, 106) shown in FIG. 1, and sample 1 (serum) arrives at the pipetting position. Upon arrival of sample 1, the preceding/current measurement sample determination part 1122 goes to step 400 in FIG. 4 and determines whether any preceding sample is present on the basis of the sample analysis requests stored in the analysis request memory 1121.

If there is no sample measured before sample 1, step 407 is reached. In step 407 sample 1 is pipetted without a special washing operation on the sample-pipetting probe 107.

Upon completion of the pipetting of sample 1, sample 2 (serum) arrives at the pipetting position. The preceding/current sample determination part 1122 then goes to step 400 and verifies what is stored in the analysis request memory 1121. Since there exists the preceding sample 1, the preceding/current sample determination part 1122 goes to step 401 and sets "1" as the condition number to be verified before going to step 402.

In step 402, the preceding/current measurement sample determination part 1122 verifies the condition table between sample types 1123. The preceding sample is serum and the current sample is urine at condition 1 in the condition table between sample types 1123, and hence, sample 2 (serum) does not apply to condition 1. In this case step 403 is followed by step 405 where other conditions 2 and 3 to be verified have been set to the table 1123. Subsequently step 406 is reached and the condition number to be verified is set to "2." The processing then returns to step 402.

Since condition 2 is the case where the preceding sample is serum and the current sample is CSF, sample 2 does not apply to condition 2. Thus step 403 is followed by step 405 where another condition 3 to be verified has been set to the table 1123. Subsequently step 406 is reached and the condition number to be verified is set to "3." The processing then returns to step 402.

Since condition 3 is the case where the preceding sample is urine, the preceding sample 1 (serum) does not apply to condition 3. Thus step 402 is followed by step 405 where the condition next to condition 3 has not been set. Subsequently step 407 is reached and sample 2 is pipetted the special washing operation.

Upon completion of the pipetting of sample 2, sample 3 (urine) arrives at the pipetting position. The preceding/current sample determination part 1122 then goes to step 400 and verifies what is stored in the analysis request memory 1121. Because the preceding sample 2 is found in the memory the preceding/current sample determination part 1122 goes to step 401 and sets the condition number to be verified to "1" before going to step 402.

In step 402 the preceding/current measurement sample determination part 1122 verifies the condition table between sample types 1123. The preceding sample is serum and the current sample is urine at condition 1 in the condition table between sample types 1123, and hence, sample 3 (urine) applies to condition 1. The preceding/current evaluation sample determination part 1122 thus goes from step 402 to step 403 to step 404. In step 404 the preceding/current measurement sample determination part 1122 supplies the sample-pipetting mechanism controller 1125 with a command to perform washing in pattern 1 serving as the wash type for condition 1.

Given the command to perform washing in wash pattern 1, the sample-pipetting mechanism controller 1125 searches through the washing method table of each pattern 1124 to retrieve the washing method of pattern 1 therefrom and causes the sample-pipetting probe 107 to be washed with the retrieved washing method. The washing involves the ordinary washing of the sample-pipetting probe 107 supplemented with automatic execution of the washing operation given under condition 1 of FIG. 1, whereby the effect of carry-over from the preceding sample 2 (serum) to sample 3 (urine) is prevented to improve the accuracy of the result of measurement of sample 3 (urine). Sample 3 starts to be pipetted after this washing operation.

Upon completion of the pipetting of sample 3, sample 4 (urine) then arrives at the pipetting position. The above-described determination process shown in FIG. 4 is carried out after the arrival of sample 4. None of conditions 1 through 3 applies to this case since the preceding sample is sample 3 (urine) and the current sample to be measured is sample 4 (urine).

As a result, the decisions in steps 400, 401, 402, 403, 405, and 406 are carried out before step 407 is reached. In step 407 the special washing operation is not performed and sample 4 starts to be pipetted.

Upon completion of the pipetting of sample 4, sample 5 (serum) arrives at the pipetting position. The above-described determination process shown in FIG. 4 is carried out after the arrival of sample 5. None of conditions 1 through 3 applies to this case since the preceding sample is sample 4 (urine) and the current sample to be measured is sample 5 (serum).

As a result, the decisions in steps 400, 401, 402, 403, 405, and 406 are carried out before step 407 is reached. In step 407 the special washing operation is not performed and sample 5 starts to be pipetted.

Whereas it was explained above that the determination described in FIG. 4 is performed on the sample that arrives at the pipetting position on the pipetting line 106, the pipetting position is not limited to be somewhere on the pipetting line 106.

For example, where the sample diluted in the reaction vessel 113 is to be pipetted to another reaction vessel 113 with the use of the sample-pipetting probe 107, the pipetting position may be arranged to be where the reaction vessel 113 is located and the determination flow described in FIG. 4 may be executed accordingly.

In a case in which the sample of an effect-exerting type is to be pipetted following the above-mentioned dilution, it may be determined that the concentration of the affected item is lowered through the dilution of the sample and that the washing operation need not be inserted. In that case, even if some of the washing setting conditions in FIG. 2 does apply, the sample may be pipetted without execution of the washing operation described in FIG. 2(B) so as to suppress the rising running costs stemming from excess washing operations involving wasteful use of detergents and water, thereby preventing a decline in analysis throughput.

In addition to the above case where the sample is diluted, there may be a case where a sample of an effect-exerting type is to be pipetted following the sample to be measured again. In this case, if the concentration of the item affected by the result of the preceding measurement is so low that little effect is expected even without the washing operation to be inserted, the sample may be pipetted without execution of the washing operations described in FIG. 2(B) even if some of the washing setting conditions in FIG. 2 does apply.

Where pipetting is not carried out continuously, the sample-pipetting probe of the automatic analyzer is generally subjected to the washing operation with water on the inner and outer walls of the pipetting nozzle for the purpose of preventing the pipetting nozzle tip of the sample-pipetting probe from drying. The washing settings in FIG. 2 are thus supplemented with settings for determining whether the effect of carry-over can be avoided with a given frequency of the washing operation using water on the pipetting nozzle. When it is determined that the effect of carry-over can be avoided, the washing operation described in FIG. 2(B) is not performed even if some of the washing setting conditions in FIG. 2 does apply. Instead, the washing operation with water may be carried out on the inner and outer walls of the pipetting nozzle a predetermined number of times before the sample is pipetted, whereby the drop in analysis throughput will be prevented.

This method is explained below with reference to FIGS. 7, 8 and 9.

Figure 7:
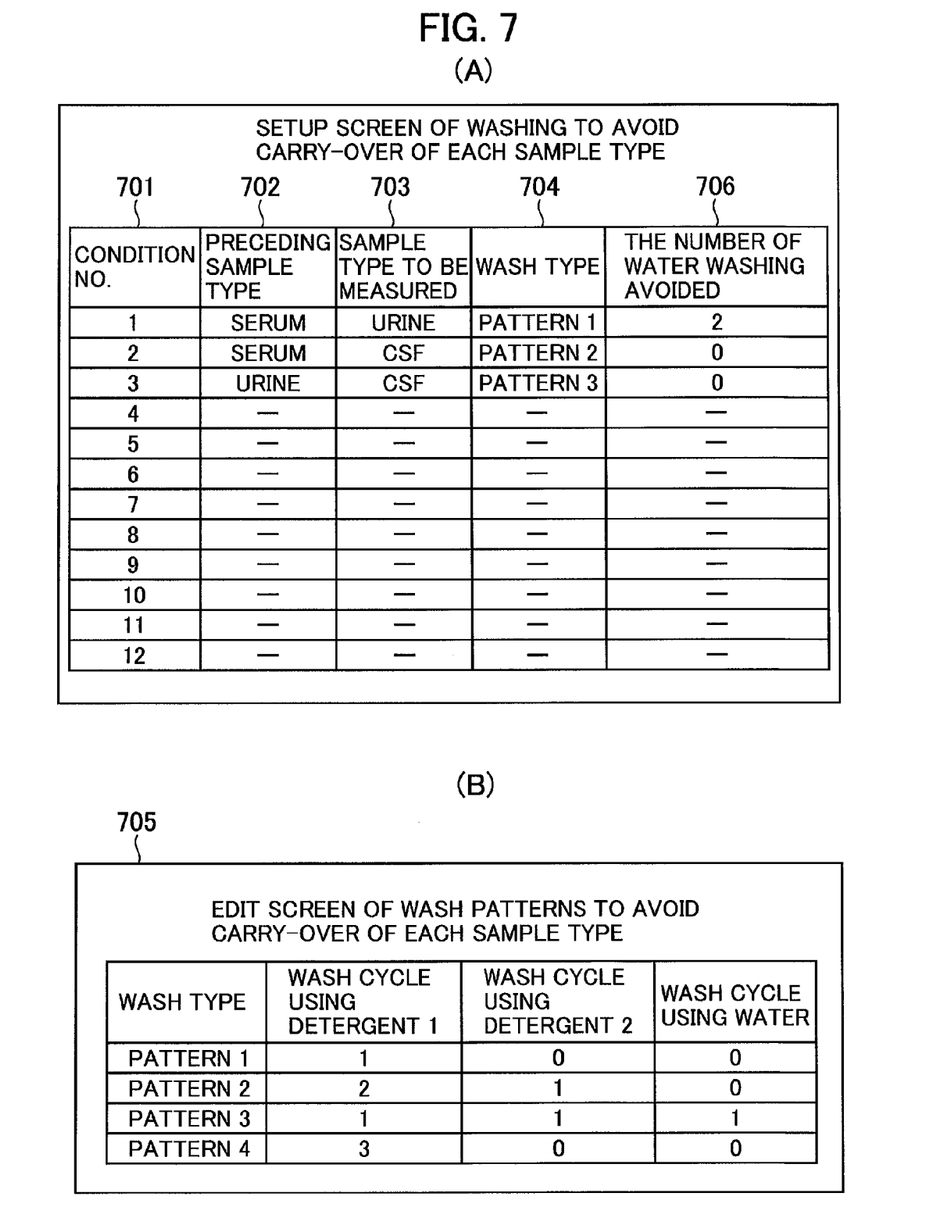
FIG. 7 is a diagram showing the screen examples of FIG. 2 in which to set whether to insert a special washing operation, in addition to the settings for determining whether washing is deficient on the basis of the number of times washing is carried out with water where pipetting is not continuous.

FIG. 7 is a diagram showing the washing setup screen in FIG. 2 supplemented with settings for determining whether the washing operation is unnecessary with the wash pattern set on the basis of the number of times washing is carried out with water where pipetting is not continuous.

In FIG. 7(A), "2" is set to a water washing cycle (706), for example, if the effect on the concentration of an ingredient in the urine sample can be averted by washing the pipetting nozzle with water twice by the time the type is switched from serum (preceding sample) to urine (current sample). With regard to the other conditions, if the effect cannot be avoided through execution of the washing with water of the pipetting nozzle a plurality of times, "0" is set to a the number of water washing avoided (706) to cancel the setting.

Figure 8:
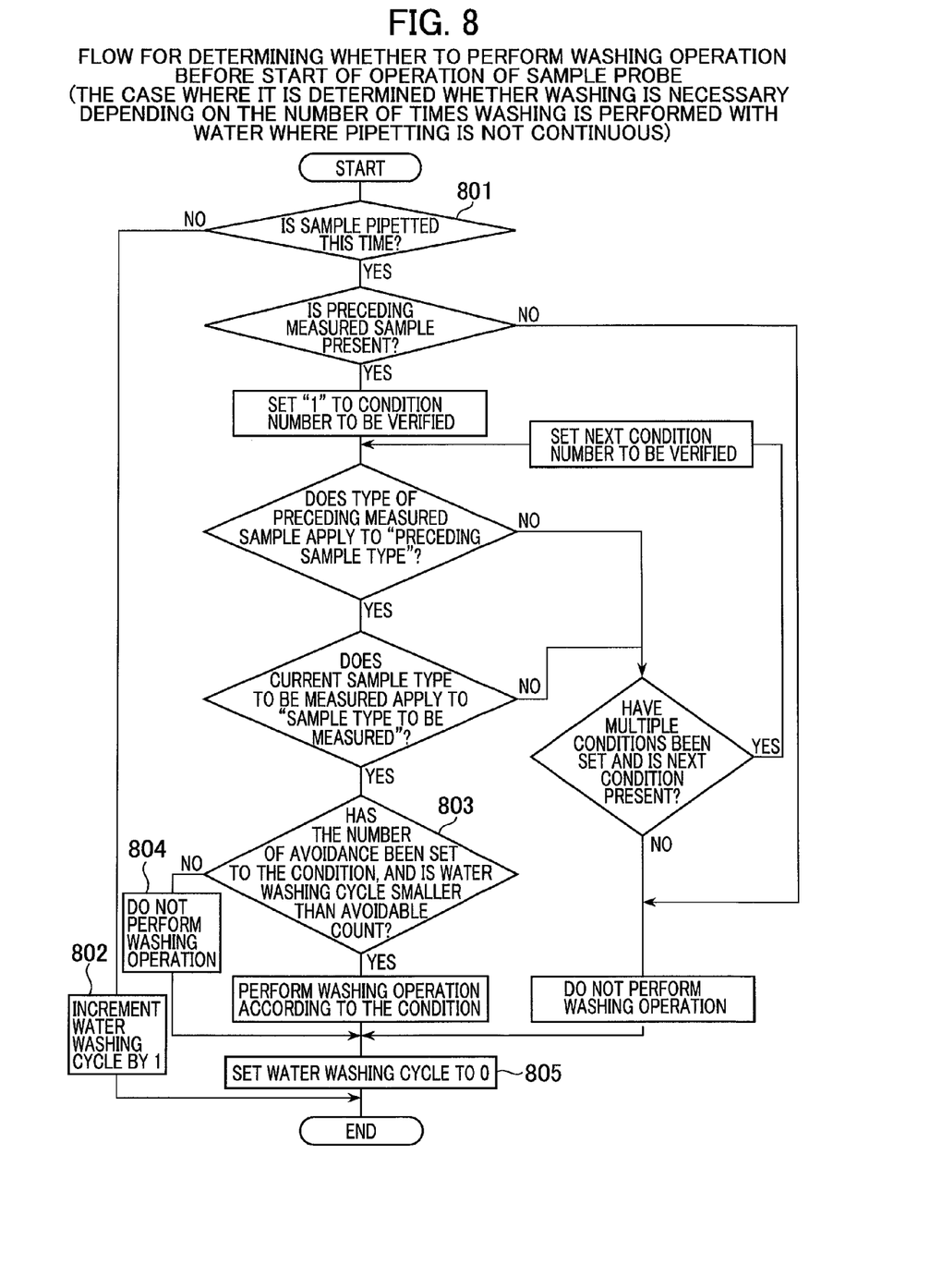
FIG. 8 is a flowchart of processing in FIG. 4 for determining whether to insert the washing operation to prevent carry-over between samples, in addition to the processing for determining whether to insert the washing operation on the basis of the number of times washing is performed with water where pipetting is not continuous.

FIG. 8 is a flowchart of processing in FIG. 4 for determining whether to insert the washing operation to prevent carry-over between samples of different types before the sample that has arrived starts to be pipetted, the processing being supplemented with steps (802) and (805) for storing the frequency of washing with water where pipetting is not performed continuously and with step (803) for determining the water washing cycle (706) set in FIG. 7. FIG. 9 is a diagram chronologically showing how the sample-pipetting probe 107 is controlled by this method.

Figure 9:
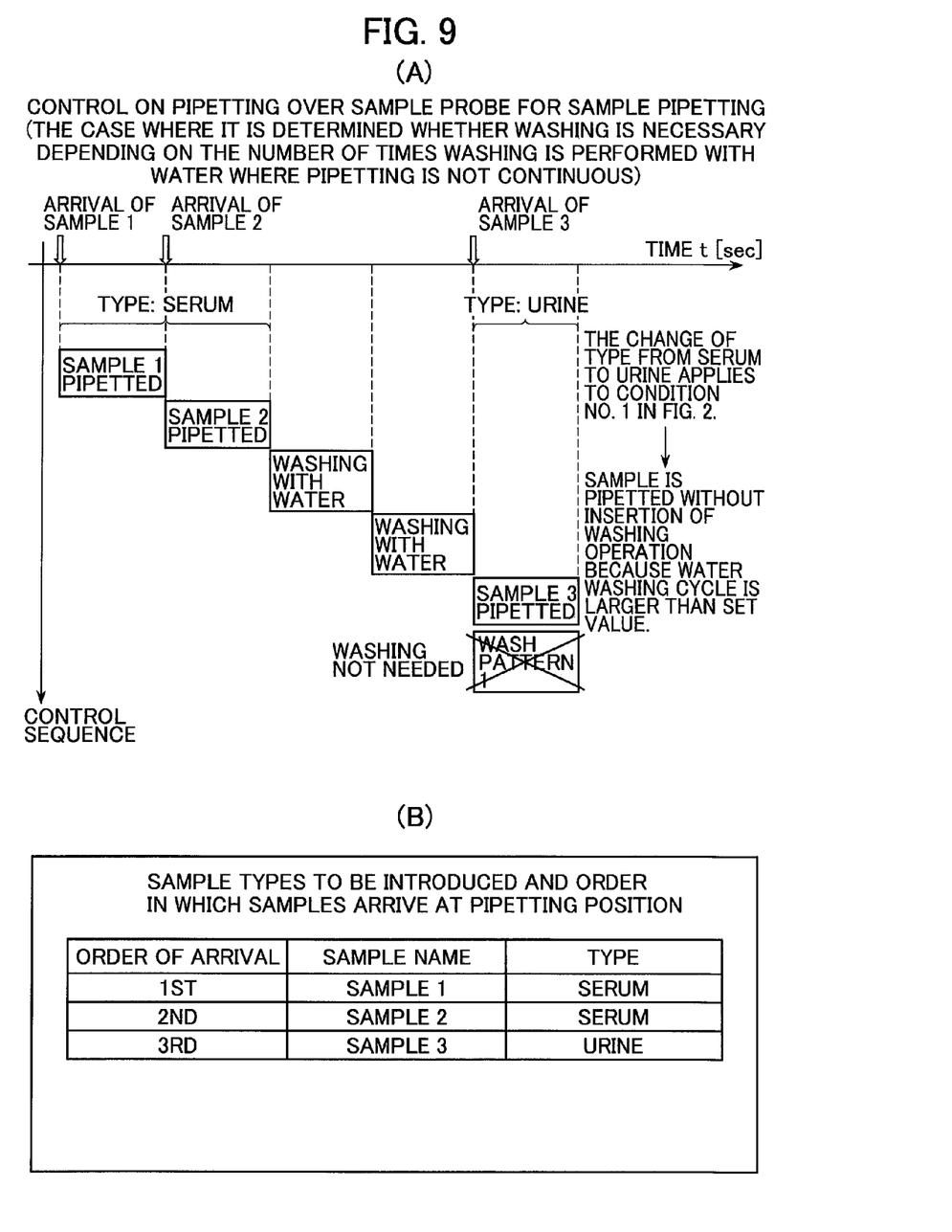
FIG. 9 is a diagram chronologically showing how the sample-pipetting probe is controlled on the basis of the order in which samples arrive and of the type, using the method of determining whether to perform washing on the basis of the number of times washing is performed with water where pipetting is not continuous.

In FIG. 9, the control from the start of measurement up to the pipetting of sample 1 (serum) and sample 2 (serum) are the same as with the method described above in reference to FIG. 3.

The pipetting nozzle is washed with water when the sample 3 (urine) does not arrive and no sample is pipetted by the sample probe 107 at the pipetting timing. The determination shown in FIG. 8 is carried out in this case. It has been determined in step 801 that no sample is pipetted this time, and step 802 is then reached. After the "water washing cycle" is incremented by 1 in step 802, the processing is terminated.

At the next timing, sample 3 (urine) does not arrive and no sample is pipetted by the sample probe 107 at the pipetting timing, so that the pipetting nozzle is washed with water. The determination in FIG. 8 is carried out in this case, too. It is also determined in step 801 that no sample is pipetted this time, and step 802 is then reached. After the "water washing cycle" is incremented by 1 in step 802, the processing is terminated. The "water washing cycle" is 2 as a result.

Step 801 is reached next at the time of arrival of the sample 3 (urine) at the pipetting position. The condition number to be verified is set to "1" as in FIG. 4 since the sample is determined to be pipetted this time in step 801, and the condition table between sample types 1123 is verified. The preceding sample is serum and the current sample is urine at condition 1 in the condition table between sample types 1123, so that sample 3 (urine) applies to condition 1. Control is then passed to the added step 803.

The the number of water washing avoided (706) in FIG. 7 is found set in step 803, so that the the number of water washing avoided (706) of 2 is compared with the current "water washing cycle" of 2. Since the comparison reveals that the "water washing cycle" has reached the the number of water washing avoided (706) of "2" in FIG. 7, step 804 is subsequently reached. In step 804 the washing operation is not performed and the sample starts to be pipetted.

As a result, the drop in analysis throughput attributable to the inserted washing operation does not occur, and the effect of carry-over can be avoided efficiently.

Whereas the time required for the washing operation is allocated in the above-described embodiment, a system having a long pipetting cycle may replace the ordinary washing operation in which water is used following pipetting of the sample with execution of the washing operation that has been set up through the screen shown in FIG. 2, whereby the drop in analysis throughput may be prevented.

Figure 10:
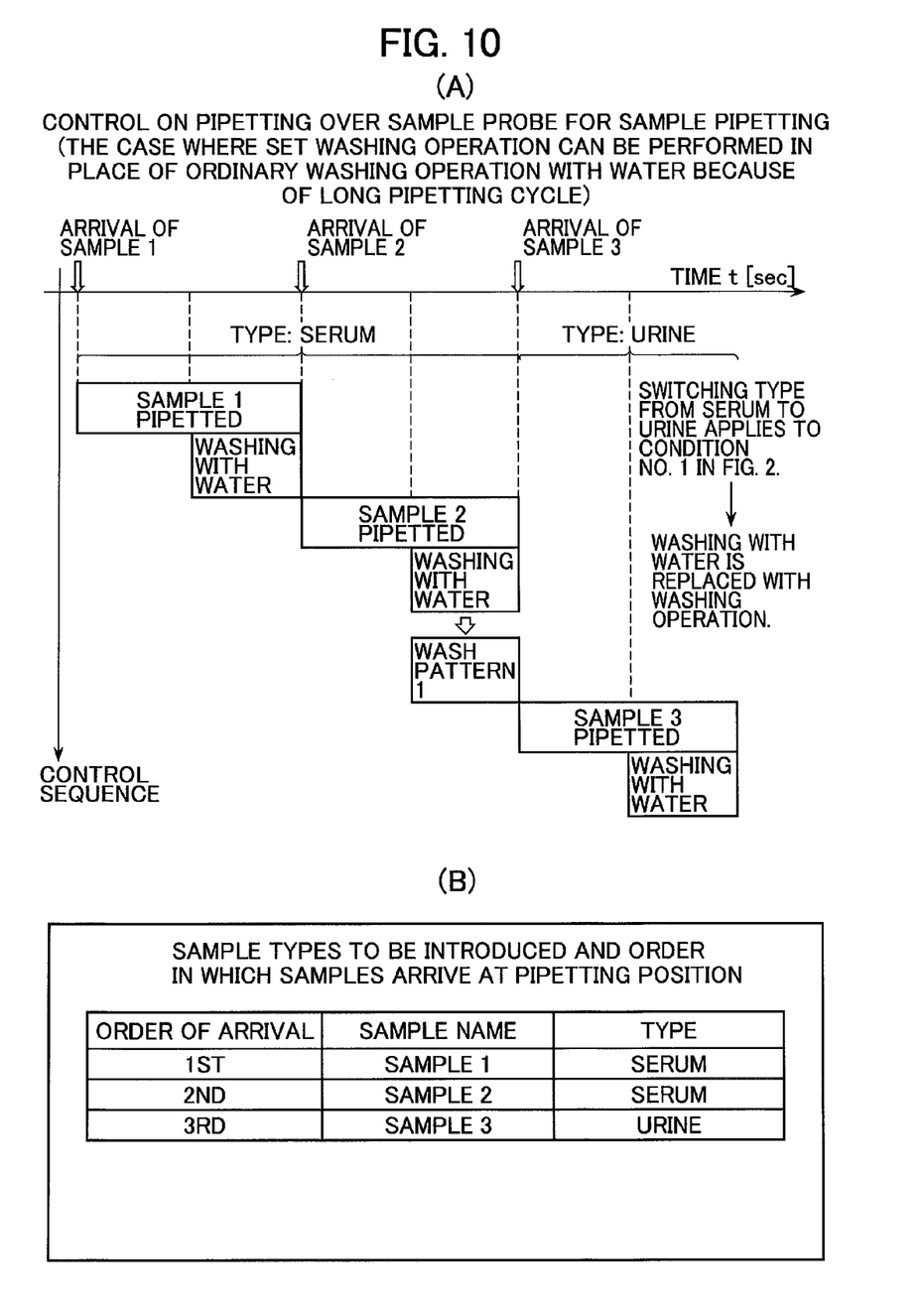
FIG. 10 is a diagram chronologically showing how the sample-pipetting probe is controlled on the basis of the sample type and the order in which samples arrive, in a system in which the ordinary washing operation in which normal water is used can be replaced with the washing operation set up through the screen of FIG. 2 because of a long pipetting cycle.

FIG. 10 is a diagram chronologically showing how the sample-pipetting probe is controlled in a system in which the ordinary washing operation where water is used can be replaced with the washing operation set up through the screen of FIG. 2 because of a long pipetting cycle.

According to the above-described method, samples are transferred via the feeder lines (101, 102, 106) in FIG. 1. When a sample arrives at the pipetting position of the sample-pipetting probe 107, step 400 in FIG. 4 is reached. In step 400, the preceding/current measurement sample determination part 1122 determines whether the preceding sample is present on the basis of the sample analysis requests stored in the analysis request memory 1121. According to this method, by contrast, the above determination is carried out on the sample expected to arrive, at the time of starting to wash with water while the sample is being pipetted as shown in FIG. 10.

In FIG. 10 the control from the start of measurement up to the pipetting of sample 1 (serum) and sample 2 (serum) is the same as with the method described above in reference to FIG. 3.

With sample 2 (serum) pipetted, the sample that arrives next is acquired at the time of starting to wash with water. In this case, the next sample to arrive is sample 3 (urine).

In step 400, the preceding/current sample determination part 1122 verifies what is stored in the analysis request memory 1121. Upon determining that there exists the preceding sample 2, the preceding/current sample determination part 1122 goes to step 401. The number of the condition to be verified is set to "1" in step 401 before step 402 is reached.

In step 402, the preceding/current measurement sample determination part 1122 verifies the condition table between sample types 1123. The preceding sample is serum and the current sample is urine at condition 1 in the condition table between sample types 1123, and hence, sample 3 (urine) applies to condition 1. The preceding/current measurement sample determination part 1122 thus goes from step 402 to step 403 and to step 404. In step 404, the preceding/current measurement sample determination part 1122 supplies the sample-pipetting mechanism controller 1125 with the command to perform washing in pattern 1 serving as the wash type for condition 1.

Given the command to perform washing in wash pattern 1, the sample-pipetting mechanism controller 1125 searches through the washing method table of each pattern 1124 to retrieve the washing method of pattern 1 therefrom, and causes the sample-pipetting probe 107 to be washed by the washing method of pattern 1 that replaces ordinary washing operation in which water is used.

As a result, sample 3 (urine) starts to be pipetted without delay while the effect of carry-over from the preceding sample 2 (serum) to sample 3 (urine) is suppressed at the same time whereby the drop in analysis throughput is prevented.

The above-described embodiment works on the method of determining whether to perform washing in the order in which samples arrive at the pipetting position. Alternatively, if the automatic analyzer is configured to allow the order of sample arrivals to be changed or to let the sample probe 107 randomly access the introduced samples, the order in which the samples arrive or are pipetted may be changed suitably so as not to carry out the washing operation set up beforehand through the screen of FIG. 2, whereby excess washing operations may be suppressed to save detergents and water and inhibit the rise in running costs and the drop in analysis throughput.

Further, whereas the time required for the washing operation is allocated with the above-described embodiment, a system having a long pipetting cycle may replace the ordinary washing operation in which water is used following pipetting of the sample with the execution of the washing operation that has been set up through the screen shown in FIG. 2, whereby the drop in analysis throughput may be prevented.

Explained next is how to calculate the amount of the wash fluid for use in the washing operations described in FIG. 2.

Figure 6:
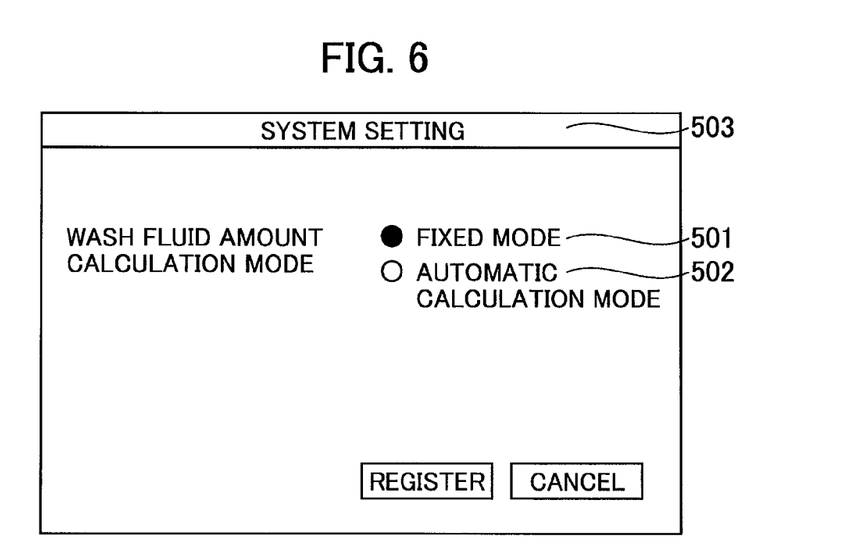
FIG. 6 is a diagram showing a typical setup screen for switching modes in which to calculate the amount of wash fluid.

FIG. 6 is a diagram showing a typical setup screen for switching modes in which to calculate the amount of wash fluid. This setup screen is the display screen of the personal computer 112.

The calculation method of the wash fluid amount for the washing operations described in FIG. 2 includes a "fixed mode 501" in which a fixed amount of wash fluid is used and an "automatic calculation mode 502" aimed at reducing the wash fluid to be used. The two modes can be switched from one to the other through a system setting screen 503 with the keyboard (input mechanism) 118.

When measurement starts with the "fixed mode 501" selected in FIG. 6, the washing operation is performed with the fixed amount of wash fluid designated for each wash pattern prior to the start of pipetting of sample 3 (urine) in FIG. 3. Generally, a maximum aspiration amount of the sample-pipetting probe 107 is set as the wash fluid amount whatever the amount of aspiration is in effect.

When measurement starts next with the "automatic calculation mode 502" selected in FIG. 6, the sequence of types (measurement starting order) should be focused. The applicable maximum aspiration amount is stored every time a sample of a new type is pipetted.

With referring to FIG. 3, suppose that 10.0 [ul] of sample 1 (serum) is aspirated and 5.0 [ul] of sample 2 (serum) is aspirated for pipetting. In this case, the maximum aspiration amount for the type of serum is set for 10.0 [ul] at the time of starting to pipette sample 3 (urine) and is stored as such into a memory (maximum aspiration amount memory 1126 shown in FIG. 5) inside the personal computer 112. (The sample-pipetting mechanism controller 1125 stores the maximum aspiration amount into the maximum aspiration amount memory 1126.)

The determination shown in FIG. 4 is subsequently performed at the time of starting to pipette sample 3 (urine). If it is determined that the washing operation indicated in FIG.

2 needs to be carried out, the wash fluid amount to be used is calculated as the stored maximum aspiration amount of 10.0 [ul] for the type of serum, and the washing operation is accordingly performed.

In this manner, the past maximum aspiration amount for samples is calculated consecutively as a minimum necessary amount of wash fluid. This averts excessive use of the wash fluid and thereby lowers the amount of the fluid used. In such cases, the effect of carry-over can still be suppressed.

According to the prevent embodiment, as described above, the method of washing the sample-pipetting probe before pipetting a sample is changed suitably depending on the type of the samples to be measured consecutively. This suppresses carry-over from a high-concentration sample to a low-concentration sample of a different type with a minimum necessary amount of washing operation regardless of the order in which the samples are introduced or arrive at the pipetting position. It is thus possible to implement an automatic analyzer and a method of washing a sample-pipetting probe whereby the accuracy of the results of measurements can be improved.

DESCRIPTION OF REFERENCE NUMERALS

101 Sample feeding part
102 Sample feeder line
103 Sample rack
104 Sample storage
105 Analysis module
106 Pipetting line
107 Sample-pipetting probe
108 Reaction disk
109 Reagent-pipetting probe
110 Reagent disk
111 Stirring mechanism
112 Personal computer
113 Reaction vessel
114 Multi-wavelength photometer
115, 116 Rinse baths for sample-pipetting probe
117 Reagent container
118 Keyboard (input mechanism)
201 Condition number
202 Preceding type setting column corresponding to condition number
203 Measurement type setting column
204 Type setting column
205 wash pattern edit screen
501 Mode for using fixed amount of wash fluid
502 Automatic calculation mode of wash fluid amount
503 System setting switching screen
1121 Analysis request memory
1122 Preceding/current measurement sample determination part
1123 Condition table between sample types
1124 Washing method table of each pattern
1125 Sample-pipetting mechanism controller
1126 Maximum aspiration amount memory
706 The number of water washing avoided

The invention claimed is:

1. An automatic analyzer for analyzing samples of a plurality of types, the automatic analyzer comprising:
a reaction disk for holding a plurality of reaction vessels;
a sample-pipetting probe for pipetting a sample, of a plurality of samples, to be measured into a reaction vessel of the plurality of reaction vessels;
a rinse bath in which the sample-pipetting probe is washed; and
a photometer configured to measure a reaction solution that includes a sample, of the plurality of samples;
a memory;
a display unit;
a controller connected to the memory, the display unit, the sample-pipetting probe, and the photometer,
wherein the controller is programmed to:
display, on the display unit, a setup screen for previously setting information of a plurality of washing methods for washing the sample-pipetting probe, the washing methods have a combination of a wash fluid type and a cleaning frequency and are based on a combination of a type of a first sample and a type of a second sample to be pipetted after the first sample,
store the information set by the setup screen and the type of the first sample and the type of the second sample, and store a predetermined number of water washing operations in association with each stored washing method,
operate the sample-pipetting probe according to a sequence of time periods,
operate the sample-pipetting probe to pipette the first sample,
operate the sample-pipetting probe to pipette the second sample after pipetting the first sample,
determine, before operating the sample-pipetting probe to pipette the second sample, a washing method, of the plurality of washing methods, of washing the sample-pipetting probe on a basis of the combination of the type of the first sample and the type of the second sample stored in the memory and the information stored in the memory previously set by the setup screen, wherein the type of the first sample is different than the type of the second sample,
upon determining that during consecutive periods of time in the sequence of time periods of operating the sample-pipetting probe, the first sample and the second sample are to be pipetted by the sample-pipetting probe:
cause a washing operation to be performed on the sample-pipetting probe by use of the rinse bath based on the combination of the wash fluid type and the cleaning frequency of the determined washing method before operating the sample-pipetting probe to pipette the second sample,
upon determining that the first sample and the second sample are not to be pipetted by the sample-pipetting probe during consecutive periods of time in the sequence of time periods of operating the sample-pipetting probe:
determine whether a number of washing operations performed on the sample-pipetting probe by use of the rinse bath using only water after operating the sample-pipetting probe to pipette the first sample is greater than or equal to the predetermined number of washing operations associated with the determined washing method,
upon determining the number of washing operations is greater than or equal to the predetermined number of water washing operations, operate the sample-pipetting probe to pipette the second sample without causing a washing operation to be performed on the sample-pipetting probe by use of the rinse bath using the combination of the wash fluid type and the cleaning frequency of the determined washing method before operating the sample-pipetting probe to pipette the second sample, and upon determining the number of washing operations is less than the predetermined number of water washing operations, cause a washing operation to be performed on the sample-pipetting probe by use of the rinse bath using the combination of the wash fluid type and the cleaning frequency of the determined washing method before operating the sample-pipetting probe to pipette the second sample.

2. The automatic analyzer according to claim 1, wherein the memory stores a table for storing a plurality of wash patterns determined from a relationship between the type of the first sample and the type of the second sample and the wash patterns are respectively stored in association with each relationship of the type of the first sample and the type of the second sample, the table further storing the combination of the wash fluid type and the cleaning frequency for each washing pattern, which determines the washing method.

3. The automatic analyzer according to claim 1, the automatic analyzer further comprising an input mechanism to select either a fixed mode in which an amount of wash fluid used in washing the sample-pipetting probe is predefined or an automatic mode in which the amount of the wash fluid is based on a maximum aspiration amount of respective aspiration amounts at least two samples consecutively pipetted by the sample-pipetting probe.

4. The automatic analyzer according to claim 2, further comprising an input mechanism configured to change, in the table, the associations of the wash patterns with the relationships between the sample types and the combination of the wash fluid type and the cleaning frequency for each washing pattern.

5. The automatic analyzer according to claim 1, wherein the controller causes a washing operation to be performed on the sample-pipetting probe by use of the rinse bath using only water when the washing method of the combination of the first sample and the second sample is not stored in the memory.

* * * * *